(12) United States Patent
Roy et al.

(10) Patent No.: US 10,716,622 B2
(45) Date of Patent: Jul. 21, 2020

(54) MEDICAL DEVICES INCLUDING HIGH STRENGTH BOND JOINTS AND METHODS OF MAKING SAME

(71) Applicant: St. Jude Medical, Cardiology Division, Inc., St. Paul, MN (US)

(72) Inventors: Pianka Roy, Irvine, CA (US); Terry Sterrett, Huntington Beach, CA (US); Allyn Jensrud, Burnsville, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 0 days.

(21) Appl. No.: 16/213,207

(22) Filed: Dec. 7, 2018

(65) Prior Publication Data

US 2019/0167345 A1 Jun. 6, 2019

Related U.S. Application Data

(62) Division of application No. 14/600,705, filed on Jan. 20, 2015, now Pat. No. 10,182,863.
(Continued)

(51) Int. Cl.
*A61B 18/14* (2006.01)
*A61M 25/00* (2006.01)
*A61B 18/00* (2006.01)
*A61B 17/00* (2006.01)
*A61B 34/20* (2016.01)

(52) U.S. Cl.
CPC .............. *A61B 18/1492* (2013.01); *A61B 2017/00526* (2013.01); *A61B 2018/00351* (2013.01); *A61B 2018/00577* (2013.01); *A61B 2018/00839* (2013.01); *A61B 2034/2051* (2016.02); *A61B 2218/002* (2013.01); *A61M 25/001* (2013.01)

(58) Field of Classification Search
CPC ...... A61B 18/1492; A61B 2018/00577; A61B 18/1477; A61M 25/001
See application file for complete search history.

(56) References Cited

U.S. PATENT DOCUMENTS 5,423,811 A 6/1995 Imran et al.
5,810,876 A 9/1998 Kelleher
(Continued)

FOREIGN PATENT DOCUMENTS

EP 0985423 A2 3/2000
EP 1008327 A2 6/2000
(Continued)

*Primary Examiner* — Christopher T Schatz
(74) *Attorney, Agent, or Firm* — Armstrong Teasdale LLP

(57) ABSTRACT

The present disclosure relates generally to medical devices, and more specifically to ablation catheters including bond joints formed to have improved strength and resistance to failure during use. In many embodiments an expanded bond-joint length and area and gap filling are used to increase the strength of the bond joint while decreasing relative variability. The bond joint length area is increased in a controlled manner so as to increase the overall strength of the bond joint by shifting the failure mode from the bond joint to a stronger area of the ablation catheter, such as the catheter shaft. Related methods of manufacturing such ablation catheters (or other medical devices including a bond joint) are also disclosed and described herein.

9 Claims, 7 Drawing Sheets

Related U.S. Application Data

(60) Provisional application No. 61/930,648, filed on Jan. 23, 2014.

(56) References Cited

U.S. PATENT DOCUMENTS

| | | |
|---|---|---|
| 5,961,498 A | 10/1999 | Wiesendanger |
| 6,006,123 A | 12/1999 | Nguyen et al. |
| 6,569,114 B2 | 5/2003 | Ponzi et al. |
| 7,674,251 B2 | 3/2010 | Kelley |
| 8,187,267 B2 | 5/2012 | Pappone et al. |
| 2006/0241366 A1 | 10/2006 | Falwell et al. |
| 2007/0270791 A1* | 11/2007 | Wang .......... A61B 18/148 606/41 |
| 2009/0125016 A1 | 5/2009 | Wang et al. |
| 2010/0268251 A1 | 10/2010 | Chen et al. |
| 2012/0029504 A1 | 2/2012 | Afonso et al. |

FOREIGN PATENT DOCUMENTS

| | | |
|---|---|---|
| JP | H05182999 A | 8/1993 |
| JP | 200-197641 A | 7/2000 |
| JP | 2002-119519 A | 4/2002 |
| JP | 2009-208314 A | 9/2009 |

\* cited by examiner

MEDICAL DEVICES INCLUDING HIGH STRENGTH BOND JOINTS AND METHODS OF MAKING SAME

CROSS-REFERENCE TO RELATED APPLICATIONS

This application is a divisional of U.S. application Ser. No. 14/600,705, filed 20 Jan. 2015, which claims the benefit of U.S. provisional application No. 61/930,648, filed 23 Jan. 2014, which are both hereby incorporated by reference as though fully set forth herein.

BACKGROUND OF THE DISCLOSURE a. Field of the Disclosure

This disclosure relates generally to medical devices and manufacturing methods for medical devices that include at least one high strength bond joint. More specifically, this disclosure relates to ablation catheters including a bond joint having high strength and increased bond joint area between an electrode tip assembly and a catheter shaft, and methods of making the ablation catheters.

b. Background Art

Electrophysiology catheters are used for an ever-growing number of medical procedures. For example, catheters are used for diagnostic, therapeutic, and ablative procedures. Typically, the catheter is manipulated through a patient's vasculature and to the intended site, such as a site within the patient's cardiovascular system, such as the heart or renal artery.

An ablation catheter typically carries one or more electrodes, which may be used for ablation, diagnosis, or the like. There are a number of methods used for ablation of desired areas, including for example, radiofrequency (RF) ablation. RF ablation is generally accomplished by transmission of radiofrequency energy to a desired target area through an electrode assembly to ablate tissue at the target site.

The ablation catheter is generally comprised of at least two separate parts that are joined together to form a single, cohesive piece. Typically, an electrode tip assembly is mated to a catheter shaft to form a final ablation catheter. To ensure that a proper fit and bond joint can be made between the outer diameter of the electrode tip assembly and the inner diameter of a catheter shaft, care must be taken to control closely and consistently the inner diameter of the catheter shaft, which may be manufactured from a polyimide or polyether block amide material, for example. Inconsistencies in the inner diameter of the catheter shaft can result in inconsistent bonding patters with the electrode tip assembly that may impact the quality and reliability of the resulting bond joint. With many materials suitable for forming the catheter shaft, it may be difficult to produce catheter shafts with uniform and consistent inner diameters.

The foregoing discussion is intended only to illustrate the present field and should not be taken as a disavowal of claim scope.

BRIEF SUMMARY OF THE DISCLOSURE

In various embodiments of the present disclosure, medical devices, such as ablation catheters, are described that include one or more bond joints that have improved strength and resistance to failure, such as cracking or breaking apart under stress. Although described primarily herein in reference to an ablation catheter that includes an adhesive bond joint between the outer diameter of an electrode tip stem and the inner diameter of a catheter shaft, it should be understood that the disclosure as set forth herein is applicable in many medical device applications where a bond joint is required to join two generally cylindrical or other-shaped components. In many embodiments, the present disclosure is particularly useful wherein the formation of a bond joint in a medical device is difficult to control due to component dimensional stack-up (i.e., interference between an outer diameter of a first component and an inner diameter of a second component), including those situations where the inner diameter of tubing or the like is difficult to precisely control.

In accordance with the present disclosure, the embodiments described herein provide a means of increasing bond joint strength while decreasing relative variability; that is, bond joint strength is improved resulting in improved reliability of the medical device. This is generally achieved by increasing the bond joint length and area in a controlled manner so as to incorporate additional structural components into the bond joint and gap fill interstitial space between components and surfaces so as to increase bond joint strength and shift the mode of failure away from the bond joint to another area of the device. In most practical applications, other areas of the medical device, such as the catheter shaft tubing for example in an ablation catheter, have a significantly greater strength and can be more easily controlled and manufactured consistently, thus providing a means of improving assembly robustness and the overall product.

The methods of the present disclosure as described herein also provide a number of desirable improvements. In many embodiments, the medical device having the improved bond joint may be manufactured using a one step process where all of the adhesive material used to form the bond joint is applied to the desired components and surfaces prior to the bond joint formation. Additionally, other embodiments provide simplified manufacturing processes that allow for the ability to utilize two different adhesive systems; for example, a first quick curing adhesive used to form an initial bond joint and then a second adhesive used to form a secondary bond joint. With these other embodiments, the secondary bond joint is not dependent (impacted) by any potential dimensional interference fit issues present in the construction materials as the secondary bond joint is independent of any upstream bond joint formation; that is, any dimensional interference fit issues have been addressed with the formation of the initial bond joint and the secondary bond joint may be formed to further secure the materials in place and increase strength. Further, these embodiments provide the additional design benefit of using a secondary adhesive as a means of tailoring a deflectable zone modulus.

The present disclosure is specifically directed to an ablation catheter comprising an electrode tip assembly having a tip stem on a proximal end, and a catheter shaft having a distal end and a proximal end. The ablation catheter includes an adhesive bond joint bonding an outer diameter of the tip stem to an inner diameter of the distal end of the catheter shaft. The adhesive bond joint extends past the tip stem toward the proximal end of the catheter shaft.

The present disclosure is further specifically directed to a medical device comprising a first cylindrical device component having a proximal end having an outer diameter and a second cylindrical device component having a distal end having an inner diameter and a proximal end. The medical device includes an adhesive bond joint bonding the outer diameter of the proximal end of the first cylindrical device component to the inner diameter of the distal end of the second cylindrical device component. The adhesive bond joint extends past the proximal end of the first cylindrical device component toward the proximal end of the second cylindrical device component.

The present disclosure is further specifically directed to a method of forming an ablation catheter comprising a catheter shaft and an electrode tip assembly. The method comprises providing an electrode tip assembly including a tip stem on a proximal end and a wire bundle attached to the tip stem; introducing an adhesive onto a circumference of the tip stem and onto the wire bundle; and introducing the tip stem and wire bundle into a distal end of a catheter shaft.

The present disclosure is further specifically directed to a method of forming an ablation catheter comprising a catheter shaft and an electrode tip assembly. The method comprises introducing an orifice into a distal end of the catheter shaft; providing an electrode tip assembly including a tip stem on a proximal end and a wire bundle attached to the tip stem and introducing a first adhesive onto a circumference of the tip stem and onto the wire bundle; introducing the tip stem and wire bundle into a distal end of a catheter shaft; and introducing a second adhesive into the orifice on the distal end of the catheter shaft.

The foregoing and other aspects, features, details, utilities, and advantages of the present disclosure will be apparent from reading the following description and claims, and from reviewing the accompanying drawings.

DETAILED DESCRIPTION OF THE DISCLOSURE

Figure 1:
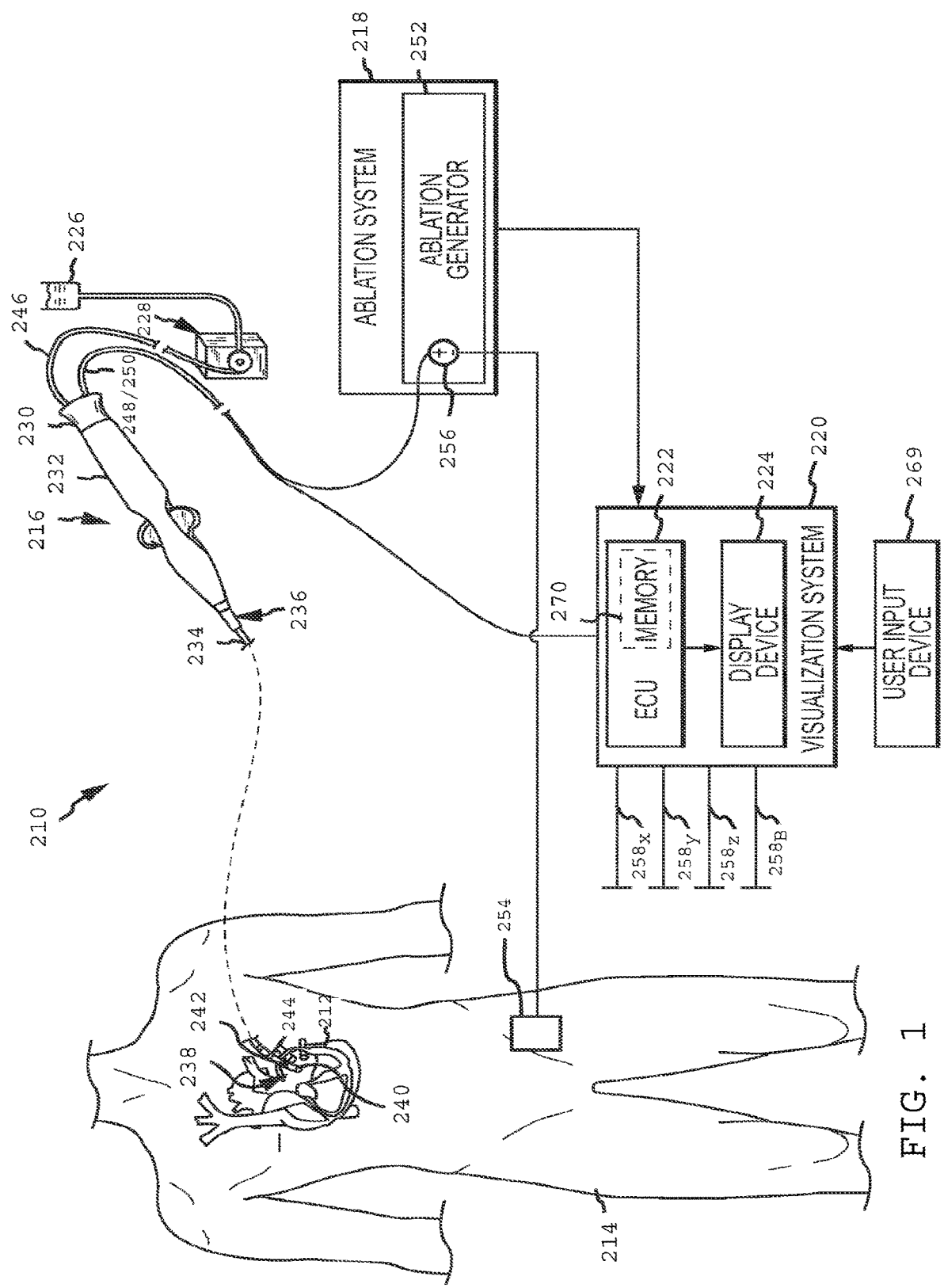
FIG. 1 is a diagrammatic view of a system for presenting information relating to lesion formation in tissue in accordance with the present teachings.

A number of medical device products require the joining of an inner diameter of one generally cylindrical member to the outer diameter of a second generally cylindrical member to form a longer, joined single continuous member for use in the device. This joining of two generally cylindrical members (or other shapes where an overlap of surfaces is required) has conventionally been done using a circumferential lap-joint including an adhesive material. In some circumstances, the forming of these types of bond joints in a reliable manner has been challenging due to the difficulty in manufacturing components (such as thermoplastic tubes) having consistent inner diameters, which results in an outer diameter-inner diameter dimensional interference during the joining of components. This dimensional interference can, in some cases, cause the bond line thickness (i.e., the gap between the two bonding surfaces) to be zero, or nearly zero, such that no adhesive material may be present to form a bond. When this occurs, only butt-joints can be formed instead of the desired circumferential lap joint. This may result in a substantially weaker bond joint that may be subject to undesirable failure and, in some cases, may result in a variation that causes the bond joint to be out of conformity with manufacturers' specifications.

Accordingly, a need exists for improved adhesive-based bond joints in medical devices, and specifically for adhesive-based bond joints in ablation catheters, wherein the bond joints exhibit increased strength, reliability, and resistance to failure. Additionally, it would be beneficial if the improved bond joints could be manufactured in a simple, reliable fashion to ensure compliance with manufacturers' specifications. Moreover, it would be desirable if the bond joints could be optionally manufactured using a combination of two adhesives to further the performance of not only the bond joint, but other characteristics of the resulting medical device as well.

In various embodiments, the present disclosure relates to medical devices, such as catheters, and specifically to ablation catheters, suitable for use in medical procedures where the ablation of tissue is required. The present disclosure is applicable to many different sized medical devices and ablation catheters, including those sized to be inserted in 6 French and 7 French openings, as well as other sized openings. In at least one embodiment, an ablation catheter includes at least one bond joint having an expanded bond-joint length and area and gap filling to increase the strength of the bond joint while decreasing relative variability. The bond joint not only includes a circumferential bond joint, but also extends past the proximal end of a first component (such as an electrode tip assembly) toward the proximal end of a second component (such as a catheter shaft) for a desired length. The bond joint length area is increased in a controlled manner so as to increase the overall strength of the bond joint by shifting the failure mode from the bond joint to a stronger area of the ablation catheter, such as the catheter shaft. Such a shift in failure mode provides a means of improving assembly robustness. Related methods of manufacturing such ablation catheters (or other medical devices including a bond joint) are also disclosed and described herein.

The disclosure and its various embodiments can now be better understood by turning to the following detailed description of numerous embodiments, which are presented as illustrative examples of the disclosure. It is expressly understood that the disclosure as set forth herein may be broader than the illustrated embodiments described below.

Referring now to the Figures, by way of background and reference, FIG. 1 illustrates one exemplary embodiment of system 210 for performing one or more diagnostic and/or therapeutic functions that includes components for presenting information representative of lesion formation in tissue 212 of body 214 during an ablation procedure performed thereon. In an exemplary embodiment, tissue 212 comprises heart or cardiac tissue within human body 214. It should be understood, however, that system 210 may find application in connection with the ablation of a variety of other tissues within human and non-human bodies.

Among other components, system 210 includes a medical device (such as, for example, catheter 216), ablation system 218, and system 220 for the visualization, navigation, and/or mapping of internal body structures. System 220 may include, for example and without limitation, an electronic control unit (ECU) 222, plurality of patch electrodes 258 ($258_x$, $258_y$, $258_z$, and $258_B$), display device 224 and user input device 269. Alternatively, ECU 222 and/or display 224 may be separate and distinct from, but electrically connected to and configured for communication with, system 220.

With continued reference to FIG. 1, catheter 216 is provided for examination, diagnosis, and/or treatment of internal body tissues such as tissue 212. In an exemplary embodiment, catheter 216 comprises an ablation catheter and, more particularly, an irrigated radio frequency (RF) ablation catheter. It should be understood, however, that catheter 216 is not limited to an irrigated catheter or an RF ablation catheter. Rather, in other embodiments, catheter 216 may comprise a non-irrigated catheter and/or other types of ablation catheters (e.g., cryoablation, ultrasound, etc.). In the exemplary embodiment wherein catheter 216 is an irrigated RF catheter, catheter 216 is connected to fluid source 226 providing a biocompatible fluid such as saline through pump 228 (which may comprise, for example, a fixed rate roller pump or variable volume syringe pump with a gravity feed supply from fluid source 226, as shown) for irrigation.

In an exemplary embodiment, catheter 216 is electrically connected to ablation system 218 to allow for the delivery of RF energy. Catheter 216 may include a cable connector or interface 230, handle 232, shaft 234 having a proximal end 236 and distal end 238 (as used herein, "proximal" refers to a direction toward the end of catheter 216 near the clinician, and "distal" refers to a direction away from the clinician and (generally) inside the body of a patient), and one or more electrodes 240 and 242 mounted in or on shaft 234 of catheter 216. In an exemplary embodiment, electrodes 240 and 242 are disposed at or near distal end 238 of shaft 234, with electrode 240 comprising an ablation electrode disposed at the extreme distal end 238 of shaft 234 (i.e., tip electrode 240), and electrode 242 comprising a positioning electrode used, for example, with the visualization, navigation, and mapping system 220. Catheter 216 may further include other conventional components such as, for example and without limitation, temperature sensor 244, additional electrodes (e.g., ring electrodes) and corresponding conductors or leads, or additional ablation elements, e.g., a high intensity focused ultrasound ablation element.

Connector 230 provides mechanical, fluid, and electrical connection(s) for cables 246, 248, and 250 extending from pump 228, ablation system 218, and visualization, navigation, and/or mapping system 220. Connector 230 is conventional in the art and is disposed at proximal end 236 of catheter 216.

Handle 232 provides a location for the clinician to hold catheter 216 and may further provide means for steering or guiding shaft 234 within body 214. For example, handle 232 may include means to change the length of a guidewire extending through catheter 216 to distal end 238 of shaft 234 to steer shaft 234. Handle 232 is also conventional in the art and it will be understood that the construction of handle 232 may vary. In another exemplary embodiment, catheter 216 may be robotically driven or controlled. Accordingly, rather than a clinician manipulating a handle to steer or guide catheter 216, and shaft 234 thereof, in particular, a robot is used to manipulate catheter 216.

In at least one embodiment, shaft 234 is an elongate, tubular, flexible member configured for movement within body 214. Shaft 234 supports, for example and without limitation, electrodes 240 and 242, associated conductors, and possibly additional electronics used for signal processing or conditioning. Shaft 234 may also permit transport, delivery and/or removal of fluids (including irrigation fluids, cryogenic ablation fluids, and bodily fluids), medicines, and/or surgical tools or instruments. Shaft 234 may be made from conventional materials such as polyurethane, and defines one or more lumens configured to house and/or transport at least electrical conductors, fluids, or surgical tools. Shaft 234 may be introduced into a blood vessel or other structure within body 214 through a conventional introducer. Shaft 234 may then be steered or guided through body 214 to a desired location such as tissue 212 with guidewires or other means known in the art.

With further reference to FIG. 1, ablation system 218 is comprised of, for example, ablation generator 252 and one or more ablation patch electrodes 254. Ablation generator 252 generates, delivers, and controls RF energy output by ablation catheter 216 and tip electrode 240 thereof, in particular. Generator 252 is conventional in the art and may comprise the commercially available unit sold under the name IBI-1500T9-CP Cardiac Ablation Generator, available from St. Jude Medical, Inc. In an exemplary embodiment, generator 252 includes RF ablation signal source 256 configured to generate an ablation signal that is output across a pair of source connectors: a positive polarity connector SOURCE (+), which may be electrically connected to tip electrode 240 of catheter 216; and a negative polarity connector SOURCE (−), which may be electrically connected to one or more of patch electrodes 254. It should be understood that the term connectors as used herein does not imply a particular type of physical interface mechanism, but is rather broadly contemplated to represent one or more electrical nodes. Source 256 is configured to generate a signal at a predetermined frequency in accordance with one or more user specified parameters (e.g., power, time, etc.) and under the control of various feedback sensing and control circuitry as is known in the art. Source 256 may generate a signal, for example, with a frequency of about 450 kHz or greater. Generator 252 may also monitor various parameters associated with the ablation procedure including, for example, impedance, the temperature at the distal tip of the catheter, applied ablation energy, and the position of the catheter, and provide feedback to the clinician or another component within system 210 regarding these parameters.

As discussed generally herein, system 210 may be used for performing one or more diagnostic and/or therapeutic functions and include components for presenting information representative of lesion formation in tissue 212 of body 214 during an ablation procedure performed thereon and is also described in U.S. Patent Publication No. 2012/0029504, published on Feb. 2, 2012, the entirety of which is hereby incorporated by reference.

Figure 2:
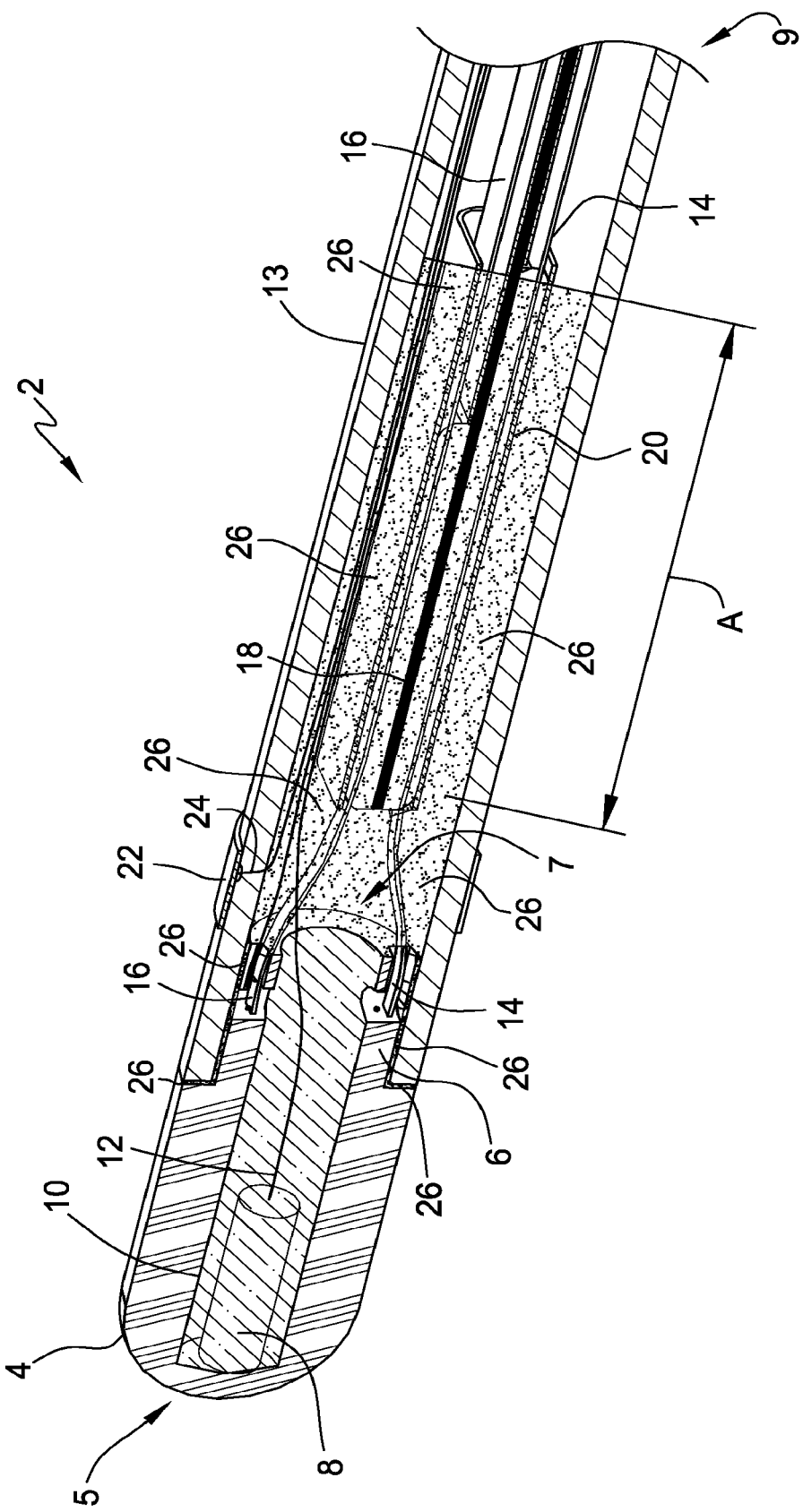
FIG. 2 depicts a cross sectional view of one embodiment of an ablation catheter including a high strength bond joint of the present disclosure.

Turning now to FIG. 2, there is shown a cross section of one embodiment of an ablation catheter 2 of the present disclosure. Although illustrated in FIG. 2 and generally herein as a non-irrigated ablation catheter, one skilled in the art based on the present disclosure will understand that the subject matter described would be equally applicable to an irrigated ablation catheter, or other ablation or diagnostic catheters (or medical devices as noted above) having a different configuration than those illustrated herein. For example, ablation catheters having different electrode tip assembly types and configurations, additional electrical components, wires, sensors, etc. are all within the scope of the present disclosure, although not specifically illustrated herein.

Referring again to FIG. 2, ablation catheter 2 generally includes electrode tip assembly 4 having distal end 5 and proximal end 7 and including tip stem 6 on proximal end 7. Electrode tip assembly 4 additionally includes thermocouple 8, thermocouple wire 12, and encapsulant 10. Ablation catheter 2 additionally includes catheter shaft 13 having proximal end 9, flat power wires 14 and 16, deflection wire 18, tubing 20, band electrode 22, and band electrode wire 24. Ablation catheter 2 further includes bond joint 26 having a Length A. Bond joint 26 (comprised of an adhesive material as described hereinbelow and illustrated in FIG. 2 as a dotted pattern) bonds electrode tip assembly 4 to catheter shaft 13 as described herein.

During an ablation procedure, electrode tip assembly 4 of ablation catheter 2 is navigated to a desired site in a body where a medical procedure, such as an ablation procedure, is to be done. In one embodiment, electrode tip assembly 4 may extend into a heart chamber of a patient. Such ablation procedures and related equipment are known to those of skill in the art.

Electrode tip assembly 4 of ablation catheter 2 is particularly suited for ablation procedures, wherein electrode tip assembly 4 is energized to deliver radio frequency (RF) waves at a site of an abnormal electrical pathway in the body. RF energy may therefore be applied to biological tissue in proximity to electrode tip assembly 4. Electrode tip assembly 4 may be fabricated from any suitable material, and in one embodiment is machined from a platinum-iridium bar (90% platinum/I 0% iridium). Electrode tip assembly 4 may be a flexible electrode tip assembly or a non-flexible electrode tip assembly, both of which are known to those of ordinary skill in the art for use in the ablation catheters described herein. While a non-flexible electrode tip assembly is illustrated, an exemplary flexible electrode tip assembly is described in U.S. Pat. No. 8,187,267, incorporated herein by reference in its entirety.

As noted above, electrode tip assembly 4 and catheter shaft 13 are connected via a bond joint that comprises an adhesive material. Catheter shaft 13 may be comprised of any suitable material known in the art including, for example, polystyrene, polyvinyl chloride, ethylene vinyl acetate, polyurethanes (urethane-based materials), nylon, polyether block amides (Pebax®), polyimides, and the like. Particularly useful materials include polyimide materials and Pebax® polyether block amides, which may optionally be reinforced as is known in the art.

Bond joint 26 (which is comprised of one or more adhesives as described herein) includes Length A along catheter shaft 13 and adhesively bonds electrode tip assembly 4 to catheter shaft 13. Bond joint 26 provides an increased bond joint length and area as compared to conventional butt joints and circumferential bond joints used to join an electrode tip assembly to a catheter shaft, and additionally provides gap filling of interstitial spaces between components and surfaces to further bond strength. As noted above, the present disclosure provides a means of increasing bond joint strength while decreasing relative variability. This improvement is achieved by increasing the bond joint area in a controlled fashion (as described hereinbelow) so as to increase the strength of the resulting bond joint by shifting the failure mode from the adhesive bond joint to the catheter shaft material, such as a polyether block amide- or polyimide-based tubing. Generally, a catheter shaft material is substantially stronger than the corresponding electrode tip assembly/catheter shaft adhesive bond joint and can be more consistently controlled, thus providing a means for improving assembly robustness.

As further illustrated in FIG. 2, bond joint 26 (and hence the adhesive that comprises the bond joint) not only bonds electrode tip assembly 4 to catheter shaft 13 through a butt joint and circumferentially around tip stem 6, but additionally creates adhesive bonding along catheter shaft 13 (Length A) and, in addition to providing bonding of tip stem 6 directly with catheter shaft 13, also includes a number of other components present in the bonding area to increase the bond joint area and improve the strength of the resulting bond joint as described herein. Bond joint 26 also provides gap filling such that interstitial space between the numerous components also contains adhesive to improve bond strength. Specifically, as shown in FIG. 2, flat power wires 14 and 16, tubing 20, thermocouple wire 12, and band electrode wire 24 are covered with adhesive within bond joint 26 to increase the strength of bond joint 26 and/or to protect such components. It will be recognized by one skilled in the art that numerous other components, wires, etc. may be located in the catheter shaft and part of the bond joint as described.

Bond joint 26 extends beyond tip stem 6 of electrode tip assembly 4 and into catheter shaft 13 toward proximal end 9 for Length A as noted above. Length A may be any suitable length for increasing the area of bond joint 26, and thus increasing the overall strength of bond joint 26. In some embodiments, Length A will be greater than or equal to about 5 millimeters, or even 6 millimeters, or even 7 millimeters, or even 8 millimeters, or even 9 millimeters, or even 10 millimeters. In other embodiments, Length A will be from about 1 millimeter to about 15 millimeters, including from about 5 millimeters to about 15 millimeters, including from about 7 millimeters to about 14 millimeters, including from about 10 millimeters to about 13 millimeters. In the areas of bond joint 26 where tip stem 6 and catheter shaft 13 are coextensive (that is, in the areas where a butt-joint and circumferential lap joint are formed), it may be useful to have a bondline thickness of at least 0.020 millimeters, or even at least 0.030 millimeters, or even at least 0.040 millimeters, or even at least 0.050 millimeters. In some embodiments, the bondline thickness may be from about 0.035 millimeters to about 0.050 millimeters. In one embodiment of the present disclosure, the bondline thickness will be from about 0.035 millimeters to about 0.050 millimeters and the Length A will be greater than or equal to about 5 millimeters.

Suitable adhesives for use in creating bond joint 26 are known in the art and may include for example, flexibilized cyanoacrylate-based adhesives, polyurethane-based adhesives, and combinations thereof. One specific example of a suitable adhesive is Biothane® 228 polyurethane (Vertellus Specialties, Inc., Indianapolis, Ind.). Another specific example of a suitable adhesive is Henkel-Hysol TRA bond FDA2 (Henkel, Rocky Hill, Conn.). In some embodiments, the suitable adhesive may have a bond strength of at least 2000 psi, or even at least 2100 psi, or even about 2175 psi. In many embodiments of the present disclosure, the resulting bond joint will have a strength that is at least two times, or even three times, as strong as compared to conventional bond joints that solely utilize a butt-joint in combination with a circumferential lap-joint.

Turning now to one embodiment for the manufacturing of ablation catheter 2, there is described a first process wherein all of the adhesive material used to form a desired bond joint is applied to the desired components prior to the joining of tip stem 6 and catheter shaft 13 to form the bond joint and resulting ablation catheter 2. In accordance with this embodiment of the present disclosure and referring now to FIG. 3, numerous components of electrode tip assembly 4 are first prepared for the application of a suitable adhesive, or combination of adhesives, and the formation of a bond joint by cleaning with a suitable cleaning agent. In at least one embodiment, each part of electrode tip assembly 4 that will be contacted with an adhesive and ultimately adhesively bonded to form the bond joint may be cleaned prior to the application of an adhesive to remove any dirt, dust, etc. so as to provide a clean surface for adhesive application.

In one embodiment, a suitable cleaning agent is used to clean surfaces 21 and 27 of tip stem 6, as well as thermocouple wire 12, flat power wires 14 and 16 and tubing 20. Thermocouple wire 12, flat power wires 14 and 16, and tubing 20, as well as any other optional wires or components present but not specifically illustrated herein may be commonly referred to as a "wire bundle" as is known in the art. Thermocouple wire 12 and tubing 20 are cleaned for any desired length, and are generally cleaned for a length at least equal to a desired Length A, as illustrated in FIG. 1 and discussed hereinabove, to ensure proper adhesion and bond joint formation. In addition to the cleaning that occurs on electrode tip assembly 4 as described, the inner diameter 15 of catheter shaft 13 may be cleaned, as illustrated in FIG. 4, prior to the formation of a bond joint for a length at least equal to a desired length A.

Suitable cleaning agents are known in the art and may include for example, organic solvents, such as alcohol like isopropanol. Other cleaning methodologies, such as plasma cleaning and others, are also within the scope of the present disclosure.

Once the components have been cleaned, a desired adhesive (not shown in FIGS. 3 and 4) may be introduced onto at least surfaces 21 and 27 of tip stem 6, as well as onto thermocouple wire 12, flat power wires 14 and 16 and tubing 20. In the illustrate embodiment, the adhesive is introduced onto tubing 20 for any desired length, generally for a distance equal to a chosen Length A (as shown in FIG. 2). The adhesive is applied to wet all bonding surfaces, as well as to fill interstitial areas present to further bond joint formation. The adhesive is generally dispensed in a controlled fashion such that the dispensed adhesive volume forms an adhesive bond joint area that provides the required bond joint strength. In one exemplary embodiment, the adhesive is applied using Henkel-Loctite® peristaltic pumps set at a pump speed of 2 with a total dispensing time of from about 0.1 seconds to about 1.5 seconds, including from about 0.5 seconds to about 1.5 seconds at each dispensing location. A suitable volume of adhesive at each dispensing location may be from about 0.001 milliliter to about 0.010 millimeters. Of course, other types of pumps or adhesive dispensing machines and pump/dispensing speeds/amounts may be used and are within the scope of the present disclosure.

Figure 4:
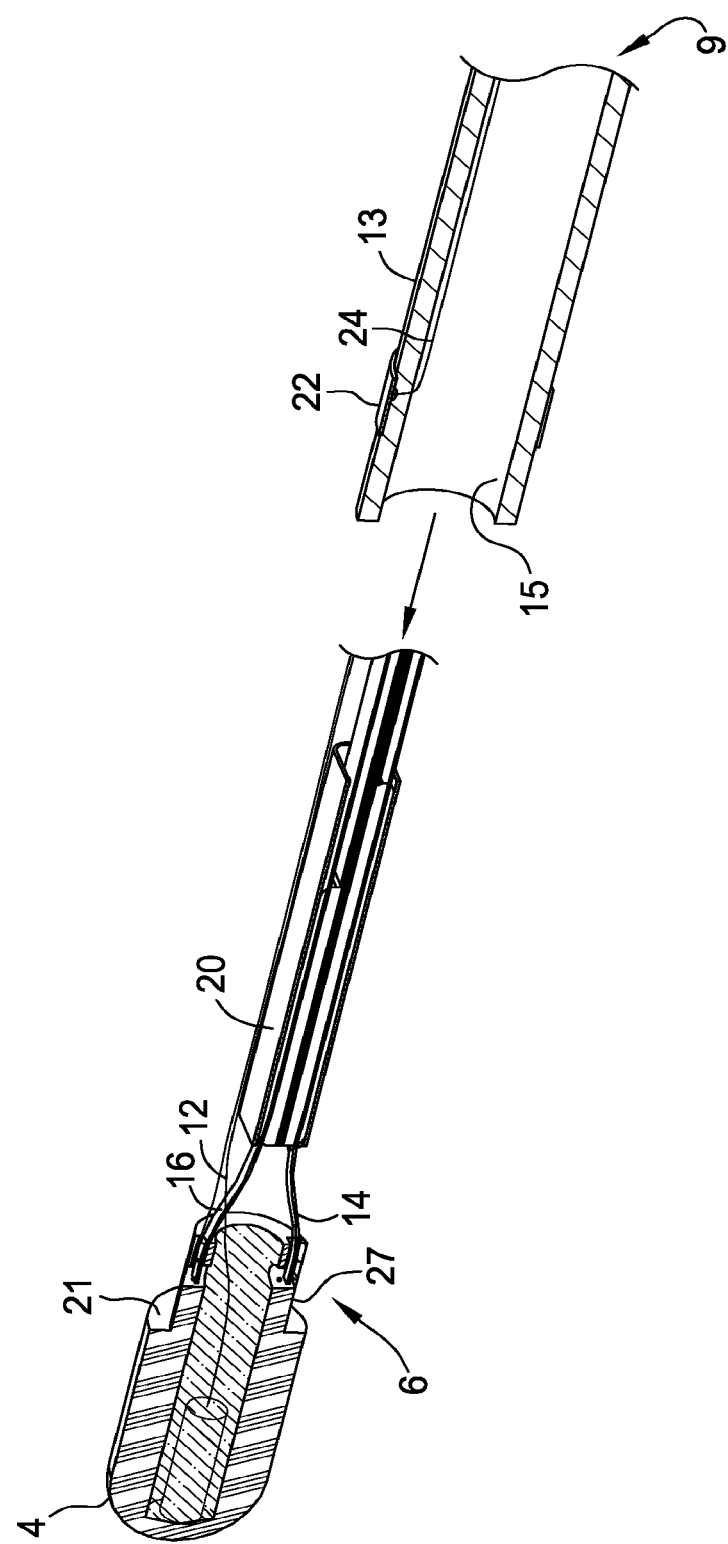
FIG. 4 depicts a cross sectional view of an electrode tip assembly and catheter shaft suitable for use in an embodiment of the present disclosure.

Once the adhesive has been introduced onto the desired surfaces and components as described above, tip stem 6 (and attached components) is inserted into catheter shaft 13, as illustrated in FIG. 4, to provide a tight fit for bond joint formation. Once properly positioned, the adhesive in the joined assembly is allowed to cure for a suitable amount of time such that the adhesive may dry and a bond joint may be formed. Curing may occur, for example, at room temperature or at an elevated temperature. Once the cure time has passed, the bond joint has been formed and the ablation catheter is ready for further processing/use.

Figure 3:
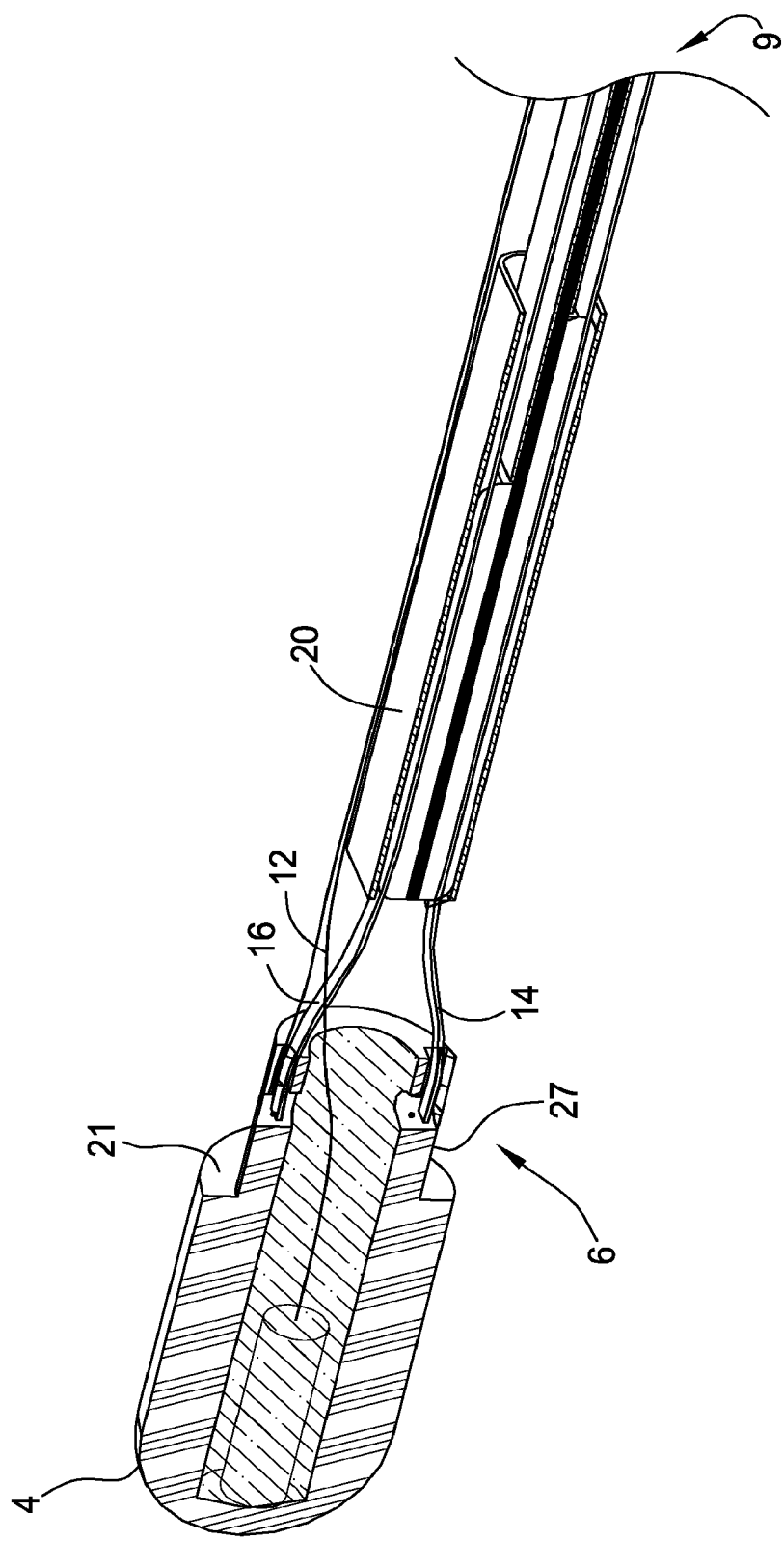
FIG. 3 depicts a cross sectional view of an electrode tip assembly suitable for use in an embodiment of the present disclosure.
Figure 5:
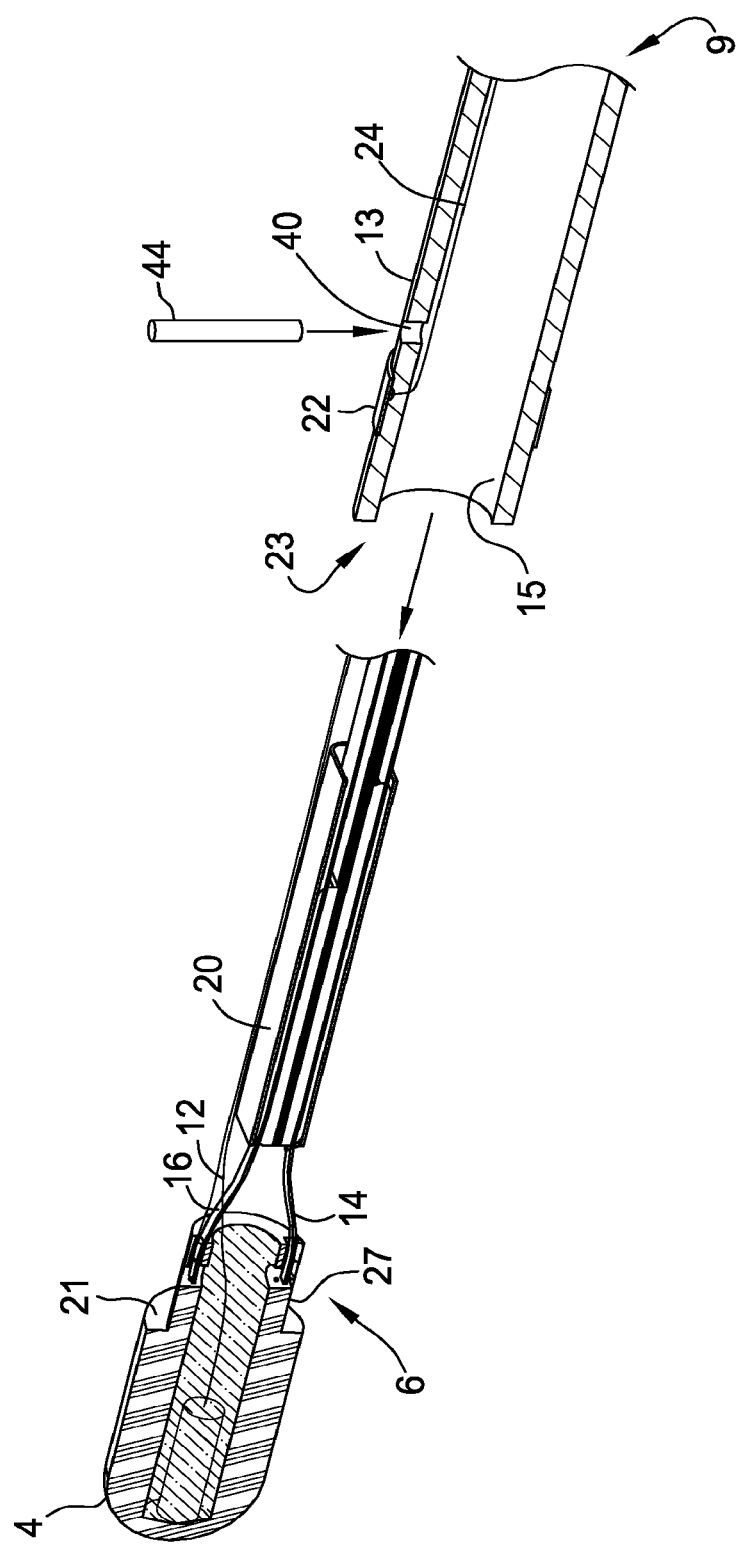
FIG. 5 depicts a cross sectional view of an electrode tip assembly and a catheter shaft including an orifice for use in an embodiment of the present disclosure.
Figure 6:
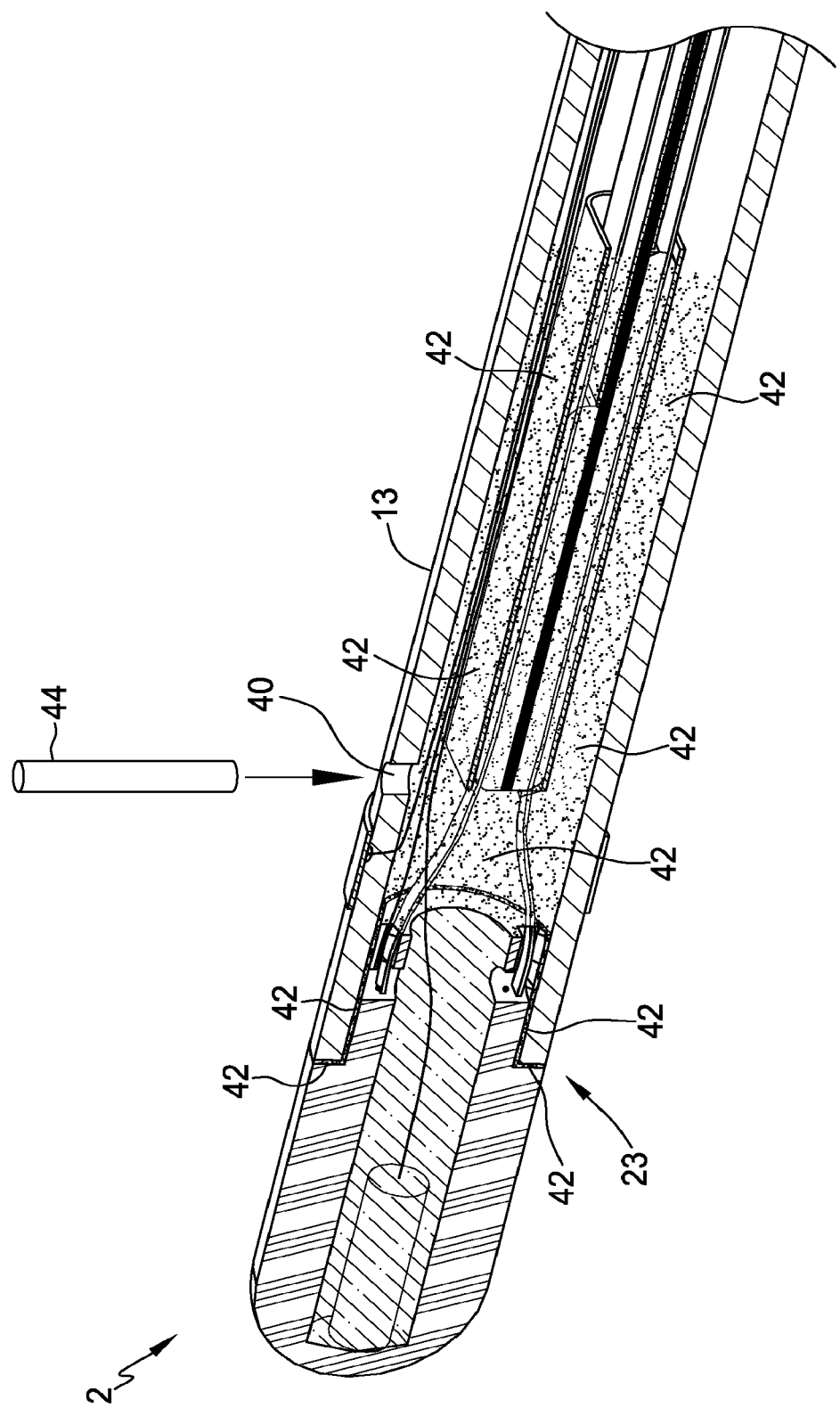
FIG. 6 depicts a cross sectional view of one embodiment of an ablation catheter of the present disclosure after a first bond joint formation.

In an alternative embodiment of the present disclosure for the manufacturing of ablation catheter 2 as shown in FIG. 1, there is described a process wherein the adhesive material for forming the improved bond joint is introduced onto the desired surfaces, components, and interstitial spaces in two separate steps of the fabrication process. In this exemplary embodiment, electrode tip assembly 4 and inner diameter 15 of catheter shaft 13 (as shown in FIGS. 3 and 4) are prepared and cleaned as described above. After cleaning (or optionally prior to the cleaning step), orifice 40 is introduced into catheter shaft 13 near distal end 23, as shown in FIGS. 5 and 6. Orifice 40 has a sufficient diameter to allow an adhesive material to be injected therethrough and into the interior of catheter shaft 13 to strengthen the bond joint as described below. In many embodiments, the orifice may have a diameter of from about 0.010 centimeters to about 0.030 centimeters, including from about 0.010 centimeters to about 0.020 centimeters. Orifice 40 is generally self-sealing after injection of the adhesive material, although it is within the scope of the present disclosure to utilize a secondary seal after the adhesive material is injected if desired.

Once orifice 40 has been introduced into catheter shaft 13 and the cleaning has been completed, a desired first adhesive (not shown) is introduced onto surfaces 21, and 27 of tip stem 6, as well as onto thermocouple wire 12, tubing 20, and flat power wires 14 and 16 as described above. Once the adhesive has been introduced onto the desired components, tip stem 6 is inserted into catheter shaft 13 as illustrated in FIGS. 5 and 6 to provide a tight fit for bond joint formation as described above.

Figure 7:
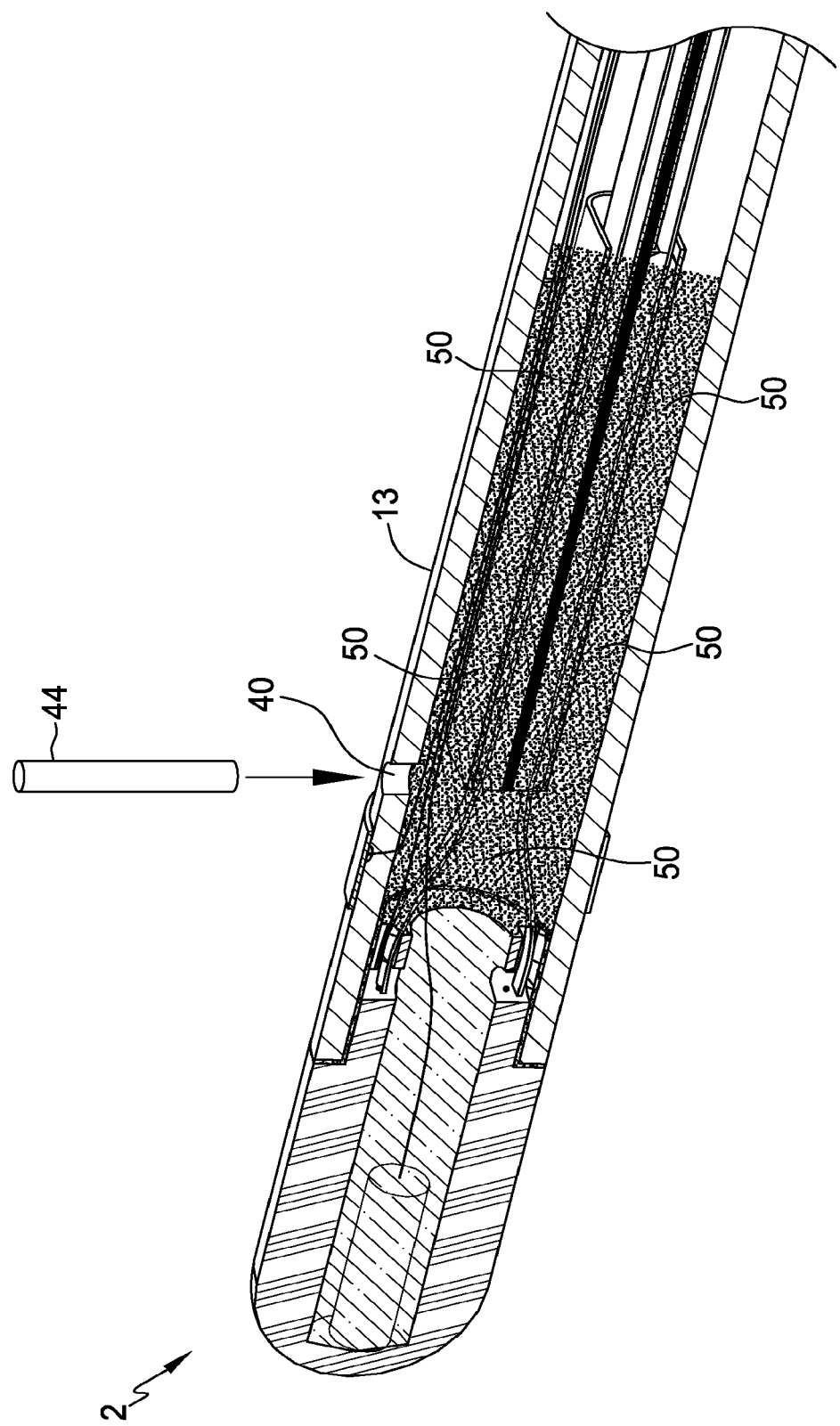
FIG. 7 depicts a cross sectional view of one embodiment of an ablation catheter of the present disclosure after a final bond joint formation.

After tip stem 6 has been inserted into catheter shaft 13 and a tight fit is formed to create an initial bond joint 42 (shown as a dotted pattern) as shown in FIG. 6, a second adhesive may then be dispensed through orifice 40 by way of tube 44 (or other means) and into catheter shaft 13 to further encapsulate and coat the components and fill interstitial space to form final bond joint 50 (as shown in heavy dotted pattern), as shown in FIG. 7. This introduction of the second adhesive will not impact any butt joint or circumferential lap joint formed using the first adhesive, but will further strengthen the area of final bond joint 50 that extends length A (as shown in FIG. 1) toward proximal end 9 of catheter shaft 13. This second adhesive may be the same as the first adhesive, or may be a different adhesive such that the bond joint is comprised of a combination of two adhesives (or, for example, a two-part epoxy system). Suitable amounts of the second adhesive are similar to the amounts described above when a single adhesive is utilized, although other amounts of adhesive are within the scope of this disclosure.

After the second adhesive has been injected into the interior of catheter shaft 13, the adhesive in the joined assembly is allowed to cure for a suitable amount of time such that the adhesive may dry and a bond joint may be formed. Curing may occur, for example, at room temperature or at an elevated temperature. Once the cure time has passed, the bond joint has been formed and the ablation catheter is ready for further processing/use.

This alternative manufacturing embodiment utilizes a two-step adhesive delivery process that provides the benefit of allowing the use of two different adhesive systems, each of which may provide a different benefit. For example, in one embodiment, a first adhesive may be used that is a quick curing adhesive used to form an initial bond joint (shown as bond joint 42 in FIG. 6) followed by a second adhesive (introduced through tube 44 as shown in FIG. 6) used to form a final bond joint (shown as final bond joint 50 in FIG.

7) to further strengthen the resulting overall bond joint. Additionally, final bond joint 50 (that is, the final bond joint formed after the injection of the second adhesive) would not be impacted by any potential dimensional interference fit issues as described above, as final bond joint 50 is independent of the upstream tip stem/catheter shaft initial bond joint formation. Moreover, this two-step adhesive delivery process provides the significant benefit of allowing for the use of a secondary adhesive as a means of tailoring the modulus of the catheter shaft in the bond joint area (i.e., the amount of flex of the catheter shaft in this area). By selecting a secondary adhesive with desired flex characteristics, the resulting overall bond joint may be tailored to impact the flex characteristics of the resulting ablation catheter shaft section to a specific specification.

Although a number embodiments of this disclosure have been described above with a certain degree of particularity, those skilled in the art could make numerous alterations to the disclosed embodiments without departing from the spirit or scope of the disclosure. It is intended that all matter contained in the above description or shown in the accompanying drawings shall be interpreted as illustrative only and not limiting. Changes in detail or structure may be made without departing from the spirit of the disclosure as defined in the claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated material does not conflict with existing definitions, statements, or other disclosed material set forth in this disclosure. As such, and to the extent necessary, the disclosure as explicitly set forth herein supersedes any conflicting material incorporated by reference herein. Any material, or portion thereof, that is said to be incorporated by reference herein, but which conflicts with existing definitions, statements, or other disclosed material set forth herein will only be incorporated to the extent that no conflict arises between that incorporated material and the existing disclosed material.

The invention claimed is:

1. A method of forming an ablation catheter comprising a catheter shaft and an electrode tip assembly, the method comprising:
   providing an electrode tip assembly including a tip stem on a proximal end and a wire bundle attached to the tip stem;
   providing tubing located in a catheter shaft;
   introducing an adhesive onto a circumference of the tip stem and onto the wire bundle and the tubing; and
   introducing the tip stem and wire bundle into a distal end of the catheter shaft, such that a distal end of the tubing is separated from the tip stem of the electrode tip assembly along a longitudinal direction of the catheter shaft, and wherein the adhesive extends past the tip stem to encapsulate and fill at least a part of the tubing towards a proximal end of the catheter shaft.

2. The method of forming an ablation catheter of claim 1 further including curing the adhesive after the tip stem and the wire bundle have been introduced into the distal end of the catheter shaft.

3. The method of forming an ablation catheter of claim 1 wherein the adhesive is present in an amount of from about 0.001 milliliters to about 0.010 milliliters.

4. The method of forming an ablation catheter of claim 1 wherein the adhesive is present in an amount of from about 0.001 milliliters to about 0.004 milliliters.

5. The method of forming an ablation catheter of claim 1 wherein the wire bundle attached to the tip stem is at least partially covered by the tubing.

6. The method of forming an ablation catheter of claim 5 wherein the tubing is covered by the adhesive.

7. A method of forming an ablation catheter comprising a catheter shaft and an electrode tip assembly, the method comprising:
   introducing an orifice into a distal end of the catheter shaft;
   providing an electrode tip assembly including a tip stem on a proximal end and a wire bundle attached to the tip stem and introducing a first adhesive onto a circumference of the tip stem and onto the wire bundle;
   introducing the tip stem and the wire bundle into the distal end of a catheter shaft; and
   introducing a second adhesive into the orifice on the distal end of the catheter shaft, wherein the first adhesive and the second adhesive form a final bond joint that extends past the tip stem to encapsulate and fill at least a part of tubing that is located within the catheter shaft towards a proximal end of the catheter shaft.

8. The method of forming an ablation catheter of claim 7 wherein the first adhesive and the second adhesive are different adhesives.

9. The method of claim 7 wherein the wire bundle is at least partially covered by the tubing.

* * * * *